(12) United States Patent
Hsiao et al.

(10) Patent No.: US 10,251,570 B2
(45) Date of Patent: Apr. 9, 2019

(54) WEARABLE ELECTRONIC DEVICE AND METHOD FOR DETECTING HEART RATE

(71) Applicant: ASUSTeK COMPUTER INC., Taipei (TW)

(72) Inventors: Yun-Tse Hsiao, Taipei (TW); Ding-Chia Kao, Taipei (TW)

(73) Assignee: ASUSTeK COMPUTER INC., Taipei (TW)

( * ) Notice: Subject to any disclaimer, the term of this patent is extended or adjusted under 35 U.S.C. 154(b) by 159 days.

(21) Appl. No.: 15/242,608

(22) Filed: Aug. 22, 2016

(65) Prior Publication Data

US 2017/0055859 A1    Mar. 2, 2017

(30) Foreign Application Priority Data

Aug. 28, 2015    (CN) .......................... 2015 1 0539641

(51) Int. Cl.
*A61B 5/024* (2006.01)

(52) U.S. Cl.
CPC ...... *A61B 5/02438* (2013.01); *A61B 5/02416* (2013.01)

(58) Field of Classification Search
CPC ........................ A61B 5/02438; A61B 5/02416
See application file for complete search history.

(56) References Cited

U.S. PATENT DOCUMENTS

| 5,431,170 A | 7/1995 | Mathews |
| 2005/0075553 A1 | 4/2005 | Sakai et al. |
| 2010/0113948 A1 | 5/2010 | Yang et al. |

FOREIGN PATENT DOCUMENTS

CN    101730503    6/2010

*Primary Examiner* — Mark Bockelman
(74) *Attorney, Agent, or Firm* — JCIPRNET

(57) ABSTRACT

A wearable electronic device comprising a wearable component and a device body is provided. The device body is connected to the wearable component. The device body includes a processor, a main light source, an auxiliary light source and a light sensor. The light sensor is electrically connected to the processor. An absorptivity to main rays from the main light source by human blood is more than twice of the absorptivity to auxiliary rays from the auxiliary light source. The light sensor detects intensities of the main rays and the auxiliary rays reflected by the human body. The processor corrects an error of the intensity of the main rays received by the light sensor according to the intensity of the auxiliary rays received by the light sensor to obtain a heart rate. A method for detecting a heart rate is also provided.

8 Claims, 2 Drawing Sheets

WEARABLE ELECTRONIC DEVICE AND METHOD FOR DETECTING HEART RATE

CROSS-REFERENCE TO RELATED APPLICATION

This application claims the priority benefit of China application serial No. 201510539641.9, filed on Aug. 28, 2015. The entirety of the above-mentioned patent application is hereby incorporated by references herein and made a part of specification.

BACKGROUND OF THE INVENTION

Field of the Invention

The invention relates to an electronic device, more specifically, to a wearable electronic device that detecting heart rates.

Description of the Related Art

With rapid development of the technology in recent years, electronic devices become small in size while having more functions. To meet the market demands for customers, wearable electronic devices, such as smart watches, are launched attractively.

On the other hand, as people pay more attention on health, the wearable electronic device is now developed to have more function in detecting physiological signals. Conventionally, a heart rate is detected according to intensity changes of the light reflected by body pulses. However, the intensity changes of the reflected light are affected by motion artifacts when a testee is in exercising. In order to remove the impact of the motion artifacts, the current wearable electronic device is usually configured with an accelerometer and a gyroscope for acquiring the motion state, and a real heart rate is obtained by signal processing. However, such a wearable electronic device is costly. Furthermore, two types of raw data (i.e., the intensity of the reflected light and the acceleration data) need to be processed in conventional method, which increases the difficulty of signal processing.

BRIEF SUMMARY OF THE INVENTION

According to one aspect of the disclosure, a wearable electronic device, comprises: a wearable component, and a device body connected to the wearable component, the device body including a processor, a main light source, an auxiliary light source and a light sensor which is electrically connected to the processor, wherein an absorptivity to main rays from the main light source by human blood is more than twice of the absorptivity to auxiliary rays from the auxiliary light source, the light sensor detects intensities of the main rays and the auxiliary rays reflected by the human body, and the processor corrects an error of the intensity of the main rays received by the light sensor according to the intensity of the auxiliary rays received by the light sensor to obtain a heart rate.

According to another aspect of the disclosure, a method for detecting a heart rate, comprises: exposing a human body to main rays and auxiliary rays, wherein an absorptivity to the main rays by the human blood is more than twice of the absorptivity to the auxiliary rays by the human blood; and correcting an error of a reflected light intensity of the main rays according to the reflected light intensity of the auxiliary rays to obtain a heart rate.

In sum, the wearable electronic device and the method for detecting a heart rate are provided to obtain a correct heart rate by comparing the intensity changes of the reflected light of the main rays with the intensity changes of the reflected light of the auxiliary rays.

BRIEF DESCRIPTION OF THE DRAWINGS

These and other features, aspects and advantages of the invention will become better understood with regard to the following embodiments and accompanying drawings.

DETAILED DESCRIPTION OF THE EMBODIMENTS

Embodiments of the invention are described hereinafter accompanying with the figures. The same or similar reference symbols denote the same or similar components in figures. The embodiments described hereinafter are exemplified only for illustration, but not for limiting the scope.

Figure 1:
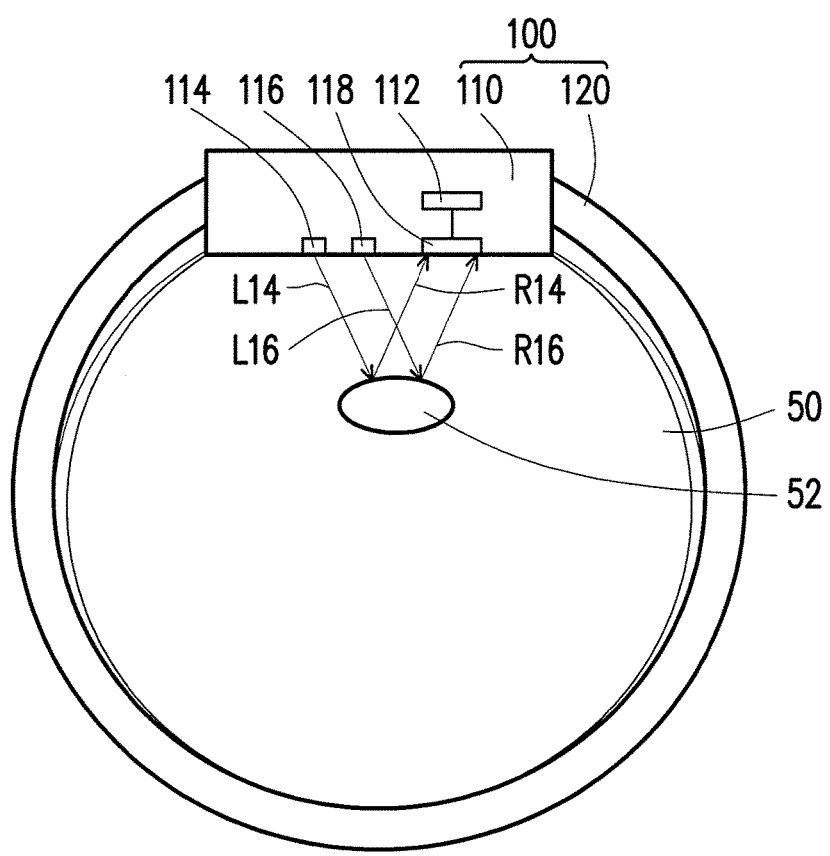
FIG. 1 is a schematic diagram showing a wearable electronic device worn on a wrist of a testee in an embodiment.

FIG. 1 is a schematic diagram showing a wearable electronic device worn on a wrist of a testee in an embodiment. Referring to FIG. 1, a wearable electronic device 100 includes a device body 110 and a wearable component 120. The device body 110 includes a processor 112, a main light source 114, an auxiliary light source 116 and a light sensor 118. The wearable component 120 is connected to the device body 110 to fix the device body 110 to a testee. In an embodiment, the wearable electronic device 100 is a watch, the device body 110 is the watch body and the wearable component 120 is the band, which is not limited herein. The processor 112 is electrically connected to the light sensor 118. An absorptivity to main rays L14 from the main light source 114 by the human blood 52 is more than twice of the absorptivity to auxiliary rays L16 from the auxiliary light source 116 by the human blood 52. The light sensor 118 detects intensities of the main rays L14 and the auxiliary rays L16 reflected by the human body 50. The processor 112 corrects an error of the intensity of the main rays L14 received by the light sensor 118 according to the intensity of the auxiliary rays L16 received by the light sensor 118 to obtain a heart rate.

Accordingly. the absorptivity to the main rays L14 from the main light source 114 by the human blood 52 is higher than that of the auxiliary rays L16. Therefore, the intensity of main reflected light R14 (the main rays L14 reflected by the human blood 52) is highly relevant to the volume changes of the human blood 52. On the other hand, the absorptivity to the auxiliary rays L16 from the auxiliary light source 116 by the human blood 52 is lower than that of the main rays L14. Therefore, the relationship between the intensity of auxiliary reflected light R16 (the auxiliary rays L16 reflected by the human blood 52) and the volume changes of the human blood 52 has low association. The main reflected light R14 and the reflected auxiliary light R16 reflect a motion state of a testee. Impact of the motion artifacts are removed from the main reflected light R14 by referring to the auxiliary reflected light R16, and thus the obtained change frequency of the volume of the human blood 52 is correct. Since the main reflected light R14 and the auxiliary reflected light R16 are both light signals, the calibration of the main reflected light R14 is not difficult via the auxiliary reflected light R16. In an embodiment, a method for detecting a heart rate includes following steps.

First, the human body 50 is exposed to the main rays L14 and the auxiliary rays L16. Second, an error of the intensity of the main reflected light R14 from the main rays L14 is corrected according to the intensity of the reflected auxiliary light R16 from the auxiliary rays L16 to obtain a heart rate. The method for detecting a heart rate is not limited to be executed by the wearable electronic device 100.

In an embodiment, the wearable electronic device 100 is configured with one light sensor 118, the manufacturing cost of the wearable electronic device 100 is reduced. In the embodiment, both the main reflected light R14 and the auxiliary reflected light R16 are detected by the light sensor 118. In an embodiment, the main rays L14 and the auxiliary light source 116 are provided alternatively by the main light source 114 and the auxiliary rays L16 respectively. In such a way, the light sensor 118 records the intensity changes of the main reflected light R14 and the auxiliary reflected light R16 alternatively according to the time points of the main rays L14 and the auxiliary light source 116 received by the light sensor 118. In an embodiment, to obtain an optimum detecting result, the wearable electronic device 100 is configured to adjust the intensities of the main rays L14 and the auxiliary rays L16 according to the testees with different skin colors.

Figure 2:
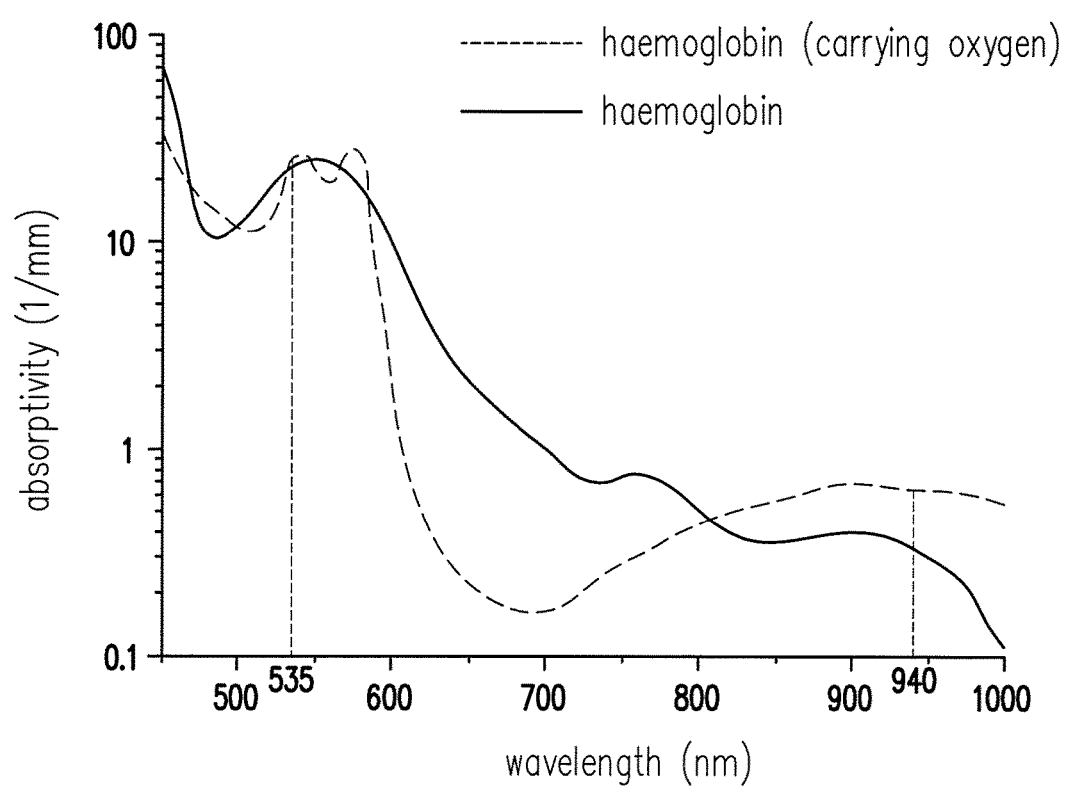
FIG. 2 is a diagram showing ray absorptivity in different wavelengths by human blood in an embodiment.

FIG. 2 is a diagram showing ray absorptivity in different wavelengths by human blood in an embodiment. Referring to FIG. 1 and FIG. 2, in the embodiment, the main rays L14 have wavelengths below 700 nm, such as blue light with wavelengths of 535 nm. The auxiliary rays L16 have wavelengths above 600 nm, such as infrared light with wavelengths of 940 nm. As shown in FIG. 2, the absorptivity to the main rays L14 with the wavelengths below 700 nm by oxyhaemoglobin and haemoglobin not carrying oxygen in the human blood is above 1/mm, however, the absorptivity to the auxiliary rays L16 with the wavelengths above 600 nm by the oxyhaemoglobin and haemoglobin not carrying oxygen in the human blood is under 1/mm. That is, the absorptivity to the main rays L14 with the wavelengths below 700 nm by the human blood is more than twice of the absorptivity to the auxiliary rays L16 with the wavelengths above 600 nm by the human blood. Therefore, the intensity of the main reflected light R14 (the main rays L14 reflected by the human blood 52) is highly relevant to the volume changes of the human blood 52, and the intensity of the auxiliary reflected light R16 (the auxiliary rays L16 reflected by the human blood 52) is slightly relevant to the volume changes of the human blood 52. Therefore, a heart rate is obtained by correcting the error of the intensity of the main rays L14 based on the intensity of the auxiliary rays L16 received by the light sensor 118.

In an embodiment, a method for detecting a heart rate includes at least following steps, which is not limited herein. First, a main frequency domain curve is transformed according to the intensity changes of the main reflected light R14 from the main rays L14 received by the light sensor 118. Second, an auxiliary frequency domain curve is transformed according to the intensity changes of the auxiliary reflected light R16 from the auxiliary rays L16 received by the light sensor 118. Then, a plurality of main peak values on the main frequency domain curve are determined, for example, 1.12 hz, 1.69 hz, 1.98 hz, 2.34 hz and 2.56 hzm, in the embodiment. A plurality of auxiliary peak values on the auxiliary frequency domain curve are determined, for example, 1.12 hz, 1.98 hz, 2.34 hz and 2.56 hz. The main peak value 1.69 hz that does not overlap with the auxiliary peak values is a target main peak value. Then, a testee's heart rate is 101.4/min calculated based on the target main peak value through following equation: 1.69×60=101.4 bpm. In an embodiment, when the maximum main peak value of the main frequency domain curve associated with the main reflected light R14 of the main rays L14 is more than five times of the maximum main peak value of the auxiliary frequency domain curve associated with the auxiliary reflected light R16 of the auxiliary rays L16, and the maximum main peak value is more than seven times of the second maximum main peak value, the maximum main peak value is the target main peak value.

In sum, in the embodiments of the wearable electronic device and the method for detecting a heart rate, the absorptivity to the main rays by the human blood is more than twice of the absorptivity to the auxiliary rays by the human blood, the intensity changes of the auxiliary reflected light from the auxiliary rays is a reference. The impact of the motion artifacts to the main reflected light are removed by referring to the auxiliary reflected light, and then a correct heart rate is obtained. The wearable electronic device is less costly and a correct heart rate is easily obtained by the error correction.

Although the invention has been disclosed with reference to certain embodiments thereof, the disclosure is not for limiting the scope. Persons having ordinary skill in the art may make various modifications and changes without departing from the scope of the invention. Therefore, the scope of the appended claims should not be limited to the description of the embodiments described above.

What is claimed is:

1. A wearable electronic device, comprising:
   a wearable component, and
   a device body connected to the wearable component, the device body including a processor, a main light source, an auxiliary light source and a light sensor which is electrically connected to the processor,
   wherein an absorptivity to main rays from the main light source by human blood is more than twice of the absorptivity to auxiliary rays from the auxiliary light source, the light sensor detects intensities of the main rays and the auxiliary rays reflected by the human body, and the processor obtains a heart rate by:
   transforming a main frequency domain curve according to changes of a reflected light intensity of the main rays received by the light sensor;
   transforming an auxiliary frequency domain curve according to changes of a reflected light intensity of the auxiliary rays received by the light sensor;
   determining a target main peak value from a plurality of main peak values of the main frequency domain curve that does not overlap with a plurality of auxiliary peak values of the auxiliary frequency domain curve; and
   obtaining the heart rate according to the target main peak value.

2. The wearable electronic device according to claim 1, wherein wavelengths of the main rays are below 700 nm and wavelengths of the auxiliary rays are above 600 nm.

3. The wearable electronic device according to claim 1, wherein the absorptivity to the main rays by the human blood is above 1/mm.

4. The wearable electronic device according to claim 1, wherein the main light source provides the main rays and the auxiliary light source provides the auxiliary rays alternatively.

5. A method for detecting a heart rate, comprising:
   exposing a human body to main rays and auxiliary rays, wherein an absorptivity to the main rays by the human blood is more than twice of the absorptivity to the auxiliary rays by the human blood;

transforming a main frequency domain curve according to changes of the reflected light intensity of the main rays;

transforming an auxiliary frequency domain curve according to changes of the reflected light intensity of the auxiliary rays;

determining a target main peak value from a plurality of main peak values of the main frequency domain curve that does not overlap with a plurality of auxiliary peak values of the auxiliary frequency domain curve; and obtaining the heart rate according to the target main peak value.

6. The method for detecting the heart rate according to claim 5, wherein wavelengths of the main rays are below 700 nm, and wavelengths of the auxiliary rays are above 600 nm.

7. The method for detecting the heart rate according to claim 5, wherein the absorptivity to the main rays by the human blood is above 1/mm.

8. The method for detecting the heart rate according to claim 5, wherein the human body is exposed to the main rays and the auxiliary rays alternatively, and the reflected light of the main rays and the auxiliary rays are detected by a light sensor.

* * * * *